United States Patent [19]
Klein

[11] Patent Number: 5,498,424
[45] Date of Patent: Mar. 12, 1996

[54] METHOD OF TREATING OBESITY

[76] Inventor: Ira Klein, 5 Windermere, Houston, Tex. 77063

[21] Appl. No.: 348,366

[22] Filed: Nov. 30, 1994

[51] Int. Cl.$^6$ ...................................................... A61K 9/20
[52] U.S. Cl. ........................ 424/464; 424/451; 514/909; 514/910
[58] Field of Search ...................... 424/464, 451, 424/423, 447, 455; 514/909, 910

[56] References Cited

U.S. PATENT DOCUMENTS

| | | | |
|---|---|---|---|
| 4,331,803 | 5/1982 | Watanabe et al. | 536/7.2 |
| 4,482,540 | 11/1984 | Gordon et al. | 424/116 |

OTHER PUBLICATIONS

Physicians' Desk Reference, *Prozac (fluoxetine hydrochloride)*, 1993, pp. 943–946.
Physicians' Desk Reference, *Pondimin (fenfluramine hydrochloride)*, 1993, pp. 1949–1950.
Physicians' Desk Reference, *Biaxin (clarithromycin)*, 1994, pp. 405–407.
Physicians' Desk Reference, *Zithromax (azithromycin)*, 1994, pp. 1789–1791.
Physicians' Desk Reference, *Eryped, Ery–Tab, E.E.S., Erythrocin, Erythromycin Base Filmtabs, Erythromycin Delayed–Release Capsules (erythromycin)*, 1994, pp. 418–426.
Merck Index, *2340, Clarithromycin*, 1989, p. 365.
Merck Index, *3626. Erythromycin*, 1989, pp. 577–578.
Stacher, G. et al., *Erythromycin Effects on Gastric Emptying, Antral Motility and Plasma Motilin and Pancreatic Polypeptide Concentrations in Anorexia Nervousa*, Feb. 1993, Gut 34:166–172.
Chaisson, R. E. et al., *Clarithromycin Therapy for Bacteremic Mycobacterium Avium Complex Disease*, 15 Dec. 1994, Annals of Internal Medicine, 121:905–911.
Wood, M. J., *The Tolerance and Toxicity of Clarithromycin*, 1991, Journal of Hospital Infection 19:39–46.
Sturgill, M. G. et al., *Clarithromycin: Review of a New Macrolide Antiobiotic with Improved Microbiologic Spectrum and Favorable Pharmacokinetic and Adverse Effect Profiles*, 1992, Annals of Pharmacotherapy, 26:1099–1108.
The Medical Letter, *Fluoxetine (Prozac) and Other Drugs for Treatment of Obesity*, Nov. 25, 1994, The Medical Letter: On Drugs and Therapeutics, 36:107–108.
Laurence, D. R. et al., *A Dictionary of Pharmacology and Clinical Drug Evaluation*, 1994, pp. 6, 228.
Agras, W. S., *Obesity and the Eating Disorders*, Oct. 1993, Scientific American Medicine, 9:1–14.
Simon, H. B. et al., *Chemotherapy for Microbial Diseases*, Mar. 1994, Scientific American Medicine, 7:1–54.
Flynn, E. H. et al., *Erythromycin. II. Des–N–methylerythromycin and N–Methyl–C$^{14}$–erythromycin*, 1955, Journal American Chemical Society, 77:3104–3106.
Bryskier, A. et al., *Structure and Activity in the New Macrolides, Azolides, and Streptogramins: Pharmacology and Clinical Applications*, 1993 (Neu, H. C. et al., eds.), pp. 3–11.
Omura, S., *Macrolide Antibiotics–Chemistry, Biology and Practice*, 1984, pp. 37–85.
"Beyond Overeating", William Ira Bennett, M.D., The New England Journal of Medicine, vol. 332, No. 10, Mar. 9, 1995, pp. 673–674.
"Finding an Obesity Gene . . . A Tale of Mice and Men", Klaus Lindpaintner, M.D., The New England Journal of Medicine, vol. 332, No. 10, Mar. 9, 1995, pp. 679–680.

*Primary Examiner*—Thurman K. Page
*Assistant Examiner*—James M. Spear
*Attorney, Agent, or Firm*—Fish & Richardson

[57] ABSTRACT

The present invention provides a simple, pharmacological method for treating obesity without risk of undesirable side effects. It has been discovered that intake of a megadose of a macrolide antibiotic creates an anorexigenic reaction in the human sufficient to result in weight loss. This method can also be used advantageously to assist non-obese persons in losing weight. The present invention relates to a method of treating obesity, comprising the steps of identifying a patient needing to lose weight and administering an appetite suppressing dose of a macrolide antibiotic compound to the patient. The dose of the macrolide antibiotic preferably ranges between a dose greater than a normal clinical dose used to treat bacterial infections and a maximum dose capable of being safely received by the patient without toxicity. In another preferred embodiment, the method includes the additional step of readministering the dose at an interval as required to maintain a desired level of appetite suppression throughout the treatment. In a preferred embodiment of the present invention, the macrolide antibiotic compound is clarithromycin.

2 Claims, No Drawings

METHOD OF TREATING OBESITY

TECHNICAL FIELD OF THE INVENTION

The present invention relates to methods of inducing weight loss in mammals, and in particular to methods of treating obesity.

BACKGROUND OF THE INVENTION

Excess adiposity, in its extreme form obesity, is generally regarded as a disorder of energy regulation. This disorder is increasingly prevalent in industrialized nations because of the abundance of food and the reduced activity levels that accompany the movement of populations from rural to urban settings. Obesity is loosely defined as an excess of body fat over that needed to maintain health.

Obesity is associated with increased morbidity and mortality. Detrimental effects of obesity on health, include an increased risk of cardiovascular disease and the associated conditions of hypertension, diabetes, and hyperlipidemia. Millions of people are clinically obese (i.e., a Body Mass Index value above the 85 1 h percentile), and, in view of the deleterious effects of obesity on health, would benefit from treatment. Additionally, many people, although not clinically obese, can improve their health and well-being by losing weight.

The pathogenesis of obesity is multifactorial and includes the control of feeding behavior, mechanisms of fat storage, the components of energy intake and expenditure, and genetic and psychological influences. Likewise, the treatment of obesity is generally multifactorial. Unfortunately, the mechanisms of fat storage and genetic influences are not, generally speaking, amenable to treatment. Moreover, the control of feeding behavior and psychological influences require protracted treatment. In addition, although the components of energy intake and expenditure are treatable, many obese individuals are resistant to or incapable of engaging in activities which significantly increase their energy expenditure. Therefore, controlling energy intake is an attractive approach for the treatment of obesity.

In addition to the voluntary reduction of food consumption, a variety of anorectic agents have been used to reduce energy intake. However, pharmacologic doses of anorectic agents such as caffeine, fenfluramine hydrochloride and fluoxetine are not without deleterious side effects. For example, caffeine has been associated with nervousness and irritability, fenfluramine hydrochloride has been associated with drowsiness, diarrhea and dry mouth, and fluoxetine has been associated with anxiety, nervousness and insomnia. While some commonly prescribed drugs (e.g., erythromycin) have an anorectic effect, this occurs in a very small percentage of patients (e.g., fewer than 3%). Moreover, this effect is associated with a general adverse reaction of the gastrointestinal system (i.e., including nausea, vomiting, abdominal pain, and diarrhea). In light of the more than thirty-four million obese adults in the United States alone, a significant need for an anorectic agent with widespread applicability and a low incidence of adverse reactions is clearly indicated.

SUMMARY OF THE INVENTION

The present invention overcomes or significantly reduces the disadvantages associated with prior methods of reducing energy intake with anorectic agents. The present invention provides a simple, pharmacological method for inducing weight loss and treating obesity in humans without undesirable side effects. It has been discovered that intake of a megadose (i.e., greater than a normal clinical dose used to treat bacterial infections) of a macrolide antibiotic creates an anorexigenic effect sufficient to produce weight loss in humans. This novel method results in weight loss without the need for any other treatment regime, but is nonetheless compatible with physical exercise, diet and behavioral modification programs.

The present invention features a method of treating obesity, including the steps of identifying a patient in need of losing body weight and administering an appetite suppressing dose of a macrolide antibiotic compound to the patient. The dose of the macrolide antibiotic preferably ranges between a dose greater than a normal clinical dose used to treat bacterial infections and a maximum dose capable of being safely received by the patient without unacceptable toxicity. In another preferred embodiment, the method includes the additional step of readministering the dose at an interval required to maintain a desired level of appetite suppression for the duration of the treatment.

In a preferred embodiment of the present invention, the macrolide antibiotic compound is clarithromycin. The preferred dose of clarithromycin is taken orally and ranges between 1250 mg and 6000 mg per day.

In a preferred embodiment of the present invention, there is disclosed a method for stimulating weight loss in a mammal, such as a human, comprising administering to the mammal a weight loss stimulating dose of a macrolide antibiotic, where the dose ranges between a dose greater than a normal clinical dose used to treat bacterial infections and a maximum dose capable of being safely received by the mammal without unacceptable toxicity. This method can also include the additional steps of readministering the dose at an interval required to obtain a desired loss of weight, or readministering the dose at an interval required to maintain a desired level and duration of appetite suppression. In this preferred embodiment of the present invention, the macrolide antibiotic compound is an erythromycin compound, such as clarithromycin. In an alternative preferred embodiment, the macrolide antibiotic compound is an azalide compound, such as azithromycin.

In a preferred embodiment, the dose of clarithromycin for a human is taken orally and ranges between 1250 mg/day and 6,000 mg/day. In an alternative preferred embodiment, the dose of clarithromycin for a human ranges between 8 mg/kg of body weight/day to 50 mg/kg of body weight/day.

In another preferred embodiment of the present invention there is disclosed a method of treating obesity in a mammal, comprising the steps of identifying a mammal in need of weight loss and administering a weight loss stimulating dose of a macrolide antibiotic compound to the mammal, where the dose ranges between a dose greater than a normal clinical dose used to treat bacterial infections and a maximum dose capable of being safely received by the mammal without unacceptable toxicity. This method also preferably can include the additional steps of readministering the dose at an interval required to obtain a desired loss of weight or readministering the dose at an interval required to maintain a desired level and duration of appetite suppression. In a preferred embodiment of this method, the macrolide antibiotic compound is an erythromycin compound, such as clarithromycin. In an alternative preferred embodiment, the macrolide antibiotic compound is an azalide compound, such as azithromycin.

In yet another preferred embodiment of the present invention, there is disclosed a method of suppressing appetite in a mammal comprising administering to the mammal an appetite suppressing dose of a macrolide antibiotic, where the dose ranges between a dose greater than a normal clinical dose used to treat bacterial infections and a maximum dose capable of being safely received by the mammal without unacceptable toxicity.

In a preferred embodiment, this method can also include the steps of readministering the dose at an interval required to obtain a desired loss of weight, or readministering the dose at an interval required to maintain a desired level and duration of appetite suppression. In a preferred embodiment of this method, the macrolide antibiotic is an erythromycin compound, such as clarithromycin. In an alternative preferred embodiment of this method, the macrolide antibiotic compound is an azalide compound, such as azithromycin.

DESCRIPTION OF THE PREFERRED EMBODIMENT

I. Method of Inducing Weight Loss and Treating Obesity

In a preferred embodiment of the present invention a method of inducing weight loss and treating obesity in mammals includes the steps of identifying a mammal in need of losing body weight and administering an appetite suppressing dose of a macrolide antibiotic compound to the mammal. The method may further include the additional step of readministering an appetite suppressing dose of the antibiotic at an interval required to maintain a desired level of appetite suppression for the duration of the treatment. The appetite suppressing dose of the macrolide antibiotic preferably ranges between a dose greater than a normal clinical dose used to treat bacterial infections and a maximum dose capable of being safely received by the mammal without unacceptable toxicity. Unacceptable toxicity is defined as that dose of a macrolide antibiotic compound which has the capacity to produce an adverse drug reaction. An adverse drug reaction is defined as a harmful or seriously unpleasant affect caused by a drug at doses intended for therapeutic affect which warrants reduction of the dose or withdrawal of the drug and/or foretells hazard from future administration. Laurence, D. R. and Carpenter, J. R., *A Dictionary of Pharmacology and Clinical Drug Evaluation*, 6, 228, 1994.

Macrolide antibiotics and macrolide-like antibiotics are described in, e.g., Bryskier, A., Agouridas, C., and Chantot, J. F., *Structure and Activity in THE NEW MACROLIDES, AZALIDES, AND STREPTOGRAMINS: PHARMACOLOGY AND CLINICAL APPLICATIONS*, 3,3–11 (Neu, H. C., Young, L. S., and Zinner, S. H., eds., 1993); and Omura, S., *Macrolide Antibiotics—Chemistry, Biology and Practice* 1984. Macrolide antibiotics include, for example, those described by Bryskier, et al., as a lipophilic molecule with a characteristic central lactone ring bearing 12 to 17 atoms, fewer than 5 and preferably no double bonds, and preferably no nitrogen atoms. Several amino and/or neutral sugars are preferably fixed to the lactone ring. One group of suitable, but somewhat atypical macrolide antibiotics, are lankacidin derivatives, 17 membered-ring macrocyclic antibiotics which do not have sugars fixed to the aglycone ring. Another group of suitable, but somewhat atypical macrolide antibiotics, are azalide compounds which contain an endocyclic nitrogen, namely azalide, within the aglycone ring. Examples of preferred macrolide antibiotics include the following synthetic, semi-synthetic or naturally occurring compounds: methymycin, neomethymycin, YC-17, litorin, erythromycin A to F, oleandomycin, roxithromycin, dirithromycin, flurithromycin, clarithromycin, davercin, azithromycin, josamycin, kitasamycin, spiramycin, midecamycin, rokitamycin, miokamycin, lankacidin, and the like. Bryskier, et al. and Omura.

As described in Watanabe, et al., U.S. Pat. No. 4,331,803, various preferred macrolide antibiotic compounds are disclosed having the formula (I)

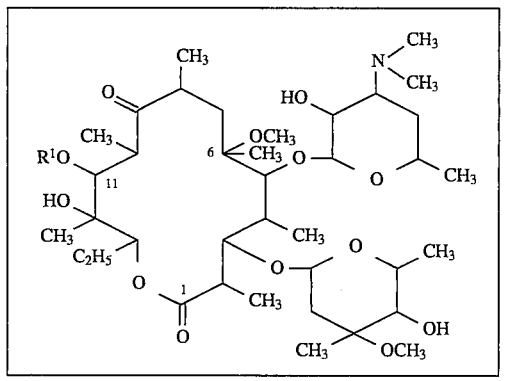

wherein $R^1$ is hydrogen or methyl, and a pharmaceutically acceptable salt thereof, having a strong antibacterial activity against Gram-positive bacteria.

The Watanabe et al. patent discloses that its invention is based on the discovery that novel compounds of formula(I) exhibit significant antibacterial activity against Gram-positive bacteria even when administered orally, contrary to other closely analogous compounds such as erythromycin A. That is, although erythromycin A is known to be a useful macrolide antibiotic having a strong activity against Gram-positive bacteria, this compound has an undesirable property that it loses rapidly the antibacterial activity by the acid in stomach when administered orally, whereupon its blood concentration remains at a low level.

Accordingly, an object of the Watanabe et al. patent was to provide novel compounds of formula (I) valuable as medicines possessing not only excellent antibacterial activity against Gram-positive bacteria and acid stability but also remarkable in vivo activity.

According to Watanabe et al., the compound of formula(I) may be prepared, for example, by the following processes. Namely, a compound of the formula (II)

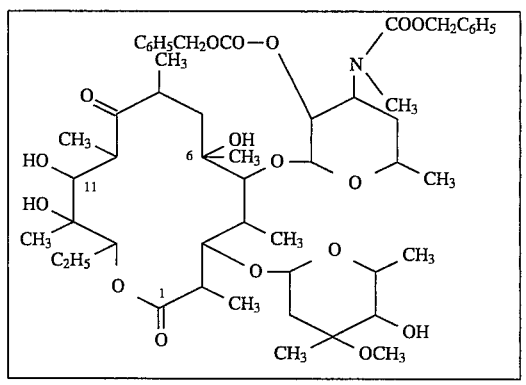

may be reacted with methyl iodide in the presence of a suitable base in a solvent to give a compound of the formula (III)

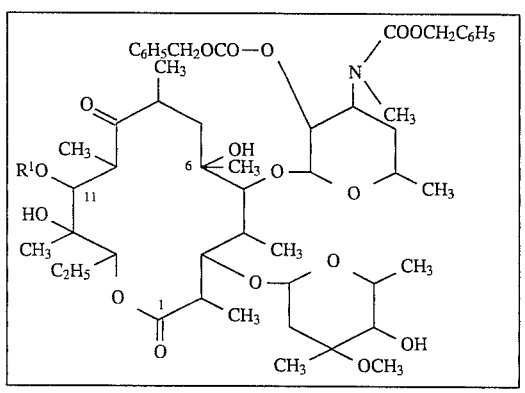

wherein $R^1$ is as defined above. In the reaction, 5–10 moles of methyl iodide and 1–2 moles of the base are employed per mole of the compound of formula(II). The reaction proceeds at temperature ranging from −78° C. to room temperature, preferably from −15+ C. to 50° C. Examples of the base are an alkali metal hydride (e.g., lithium hydride, sodium hydride or potassium hydride), an alkali metal amide (e.g., lithium amide, sodium amide or potassium amide), butyllithium or lithium diisopropylamide. Suitable solvents include polar aprotic solvents such as $N_1$N-dimethylformamide, $N_1$N-dimethylacetamide, dimethylsulfoxide or hexamethylphosphoric triamide, preferably $N_1$-dimethylformamide, dimethylsulfoxide or their mixture with tetrahydrofuran. Purification of the compound of formula(III) may be carried out by using conventional methods such as silica gel column chromatography. According to the method of E. H. Flynn et al., in *Journal of the American Chemical Society*, 77, 3104 (1955), the compound of formula(III) may be treated to remove benzyloxycarbonyl group by hydrogenolysis, and then subjected to the reductive methylation in the presence of excess amount of formaldehyde to give the compound of formula(I). Alternatively, according to Watanabe et al., the compound of formula(I) may be obtained by performing removal of benzyloxycarbonyl group and N-methylation of the compound of formula(III), at the same time. The pharmaceutically acceptable salts of the compounds of formula(I) include salts with organic acids such as an organic carboxylic acid (e.g., tartaric acid, citric acid, stearic acid or succinic acid), methanesulfonic acid, aminoethanesulfonic acid, an amino acid (e.g., aspartic acid or glutamic acid) or the like. These salts may be obtained by treating the compound of formula(I) with the corresponding acid by the conventional manners.

As disclosed in Watanabe et al., the compound of formula(II) may be prepared according to the above-described method of E. H. Flynn et at. According to Watanabe et al., the compound of the Watanabe et al. patent can be used as therapeutic agents against Gram-positive bacteria, mycoplasma and chlamydia in mammals. For these purposes, a compound of formula(I) may be administered orally or parenterally in a conventional dosage form such as tablet, capsule, powder, troches, dry mixes, ointment, suspension or solution prepare according to conventional pharmaceutical practices. These compounds of formula(I) can be administered at a dosage of from about 1 mg/kg to about 1000 mg/kg of body weight per day. The preferred dosage range is from about 5 mg/kg to about 200 mg/kg of body weight per day. According to Watanabe et al., the compounds of the Watanabe et al. invention have extremely low toxicity. The $LD_{50}$ in mice is in excess of 5000 mg/kg of body weight.

In a preferred embodiment of the present invention the macrolide antibiotic is clarithromycin. The preferred dose of clarithromycin is taken orally and is at least twice the dose normally prescribed for antibiotic indications. Clarithromycin, also known as, 6-0-methylerythromycin, has the molecular formula, $C_{38}H_{69}NO_{13}$, and a molecular weight of 747.96. Clarithromycin is commercially available from Abbott Laboratories under the trademark "BIAXIN", and is described, with other related erythromycin compounds in Watanabe, et al., U.S. Pat. No. 4,331,803 (which is incorporated herein by reference).

The structural formula of clarithromycin is:

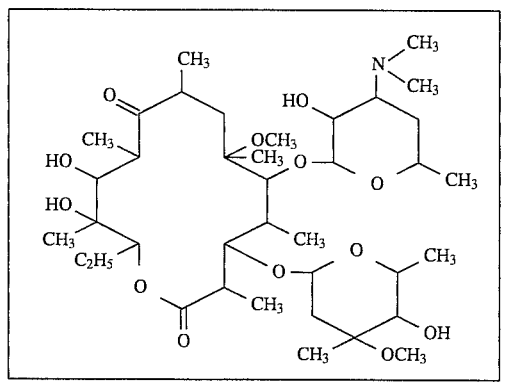

BIAXIN™ (clarithromycin) is indicated for the treatment of mild to moderate infections caused by susceptible strains of certain microorganisms in certain upper and lower respiratory tract infections, and uncomplicated skin infections. Clarithromycin is rapidly absorbed from the gastrointestinal tract after oral administration, and forms an antimicrobially active metabolite, 14-OH clarithromycin. Clarithromycin and the 14-OH clarithromycin metabolite distribute readily into body tissues and fluids. The recommended oral clarithromycin dosages for treatment of these infections ranges between 250–500 mg (every 12 hours) for a normal duration of 7–14 days. The maximum proposed human oral daily dose is reported to be 618 mg/sq m. Clarithromycin is contraindicated in patients with known hypersensitivity to clarithromycin, erythromycin, or any of the macrolide antibiotics. The majority of reported side effects observed in clinical trials of clarithromycin were of a mild and transient nature. Fewer than 3% of patients discontinued therapy because of drug-related side effects. The most frequently reported events, whether drug-related or not, were diarrhea (3%), nausea (3%), abnormal taste (3%), dyspepsia (2%), abdominal pain/discomfort (2%), and headache (2%). Most of these events were described as mild or moderate in severity. Of the reported adverse events, only 1% were described as severe (See Physicians' Desk Reference®, 405–407, 1994).

II. Therapeutic Administration of Clarithromycin

In a preferred embodiment of the present invention, a method of inducing weight loss and treating obesity in mammals includes the step of identifying a human patient in need of losing body weight. Patient identification may be accomplished by visual assessment, body weight measurement, body composition measurement, or the like. Following patient identification, a medical history is obtained with emphasis on potential adverse reactions to or contraindications for the use of macrolide antibiotics. The amount of weight to be lost is then determined based upon the patient's desires, comparison of the patient's current weight with standardized height and weight tables or other normative data, and the physician's professional judgment. Based in part upon the patient's history and goals for weight loss, a weight loss stimulating dose of a macrolide antibiotic, the interval between doses, and the duration of treatment are determined. Informed patient consent is obtained and treatment is initiated. The patient is followed at appropriate intervals during treatment and weight loss measurements, patient histories, and dose modifications, if necessary, are performed. In addition, the degree and duration of appetite suppression associated with a given dose of macrolide antibiotic is assessed. This information is used, if necessary, to modify the dose and interval of dosing required to maintain a desired level of appetite suppression throughout the treatment. In a preferred embodiment, the appetite is completely suppressed and the dosage interval is 72 hours. The results of such a treatment regime are shown in Table 1.

TABLE 1

ANORECTIC EFFECT OF CLARITHROMYCIN*

| AGE | SEX | NUMBER OF DOSES | ANOREXIA | SIDE EFFECTS | WEIGHT LOSS (LBS) | DURATION (DAYS) |
| --- | --- | --- | --- | --- | --- | --- |
| 48 | M | 4 | ++++ | ATM | 15 | 20 |
| 37 | F | 2 | ++++ | ATM | 5 | 7 |
| 42 | F | 2 | ++++ | ATM | 3 | 7 |
| 35 | F | 1 | ++++ | ATM | 2 | 3 |
| 62 | F | 1 | ++++ | ATM | 2 | 3 |
| 50 | M | 1 | – | ATM | 0 | 3 |

*All patients received 2 grams of BIAXIN ™ at 72 hour intervals. Anorexia ranges from no response (–) to extreme positive response (++++); ATM is abnormal taste in mouth.

Alternative embodiments of the present invention are described within the following claims. In addition, modes alternative to oral administration may be used (e.g., intravenous, intramuscular, intraperitoneal, topical, or the like). Moreover, macrolide antibiotic compounds other than clarithromycin may be used. For example, any of the erythromycin compounds (i.e., 14-carbon macrolides), including the novel erythromycin compounds of Watanabe, et al., (U.S. Pat. No. 4,331,803), may be used. Also, for example, homologs, analogs and derivatives of macrolide antibiotic compounds may be employed. In an alternative preferred embodiment, a macrolide antibiotic compound, such as the azalide compound azithromycin (ZITHROMAX™), can be employed. Furthermore, macrolide antibiotic compounds may be administered on a daily or intermittent basis.

What is claimed is:

1. A method for stimulating weight loss in a human comprising:

administering to said human a weight loss stimulating dose of clarithromycin, said dose being taken orally and ranging between 1250 mg/day and 6,000 mg/day.

2. A method for stimulating weight loss in a human comprising:

administering to said human a weight loss stimulating dose of clarithromycin, said dose ranging between 8 mg/kg of body weight/day to 50 mg/kg of body weight/day.

* * * * *

UNITED STATES PATENT AND TRADEMARK OFFICE
CERTIFICATE OF CORRECTION

PATENT NO.   : 5,498,424

DATED        : March 12, 1996

INVENTOR(S)  : Ira Klein

It is certified that error appears in the above-identified patent and that said Letters Patent is hereby corrected as shown below:

Column 1, line 23, please delete "851h" and insert therefore --85th--.

Column 5, line 21, please delete "-15+C." and insert therefore --15°C.--.

Signed and Sealed this

Fourth Day of June, 1996

Attest:

BRUCE LEHMAN

Attesting Officer

Commissioner of Patents and Trademarks